United States Patent [19]

Charm et al.

[11] 4,102,455

[45] * Jul. 25, 1978

[54] RADIOASSAY KIT FOR METHOD OF DETERMINING METHOTREXATE

[76] Inventors: Stanley E. Charm; Henry E. Blair, both of 136 Harrison Ave., Boston, Mass. 02111

[*] Notice: The portion of the term of this patent subsequent to Aug. 23, 1994, has been disclaimed.

[21] Appl. No.: 753,852

[22] Filed: Dec. 23, 1976

Related U.S. Application Data

[63] Continuation of Ser. No. 650,690, Jan. 20, 1976, Pat. No. 4,043,759.

[51] Int. Cl.$^2$ ................ A61B 19/00; A61K 43/00
[52] U.S. Cl. ................ 206/569; 23/253 R; 424/1
[58] Field of Search ............ 23/230 B, 253 R, 259 R; 424/1, 1.5, 12; 195/103.5 R; 206/569

[56] References Cited

U.S. PATENT DOCUMENTS

| | | | |
|---|---|---|---|
| 3,981,983 | 9/1976 | Caston et al. | 424/1.5 |
| 3,989,812 | 11/1976 | Barrett et al. | 424/1 |
| 4,043,759 | 8/1977 | Charm et al. | 424/1 |

OTHER PUBLICATIONS

Croll et al., Ed., New Techniques in Tumor Location and Radio Immuno Assay, John Wiley & Sons, N.Y., 1974.

*Primary Examiner*—Benjamin R. Padgett
*Assistant Examiner*—Christine M. Nucker
*Attorney, Agent, or Firm*—Richard P. Crowley

[57] ABSTRACT

A radioassay system for the determination of methotrexate in biological fluids based on the competitive binding of labeled and unlabeled methotrexate to the enzyme dihydrofolate reductase. Samples of unknown methotrexate level are mixed with $I^{125}$ labeled methotrexate. A portion of the total methotrexate present is bound by the addition of enzyme, and the unbound methotrexate is removed with charcoal. The level of bound $I^{125}$ labeled methotrexate is measured in a gamma counter. To calculate the methotrexate level of the unknown samples, the displacement of bound labeled methotrexate caused by the unknowns is compared to the displacement caused by known methotrexate standards.

8 Claims, 1 Drawing Figure

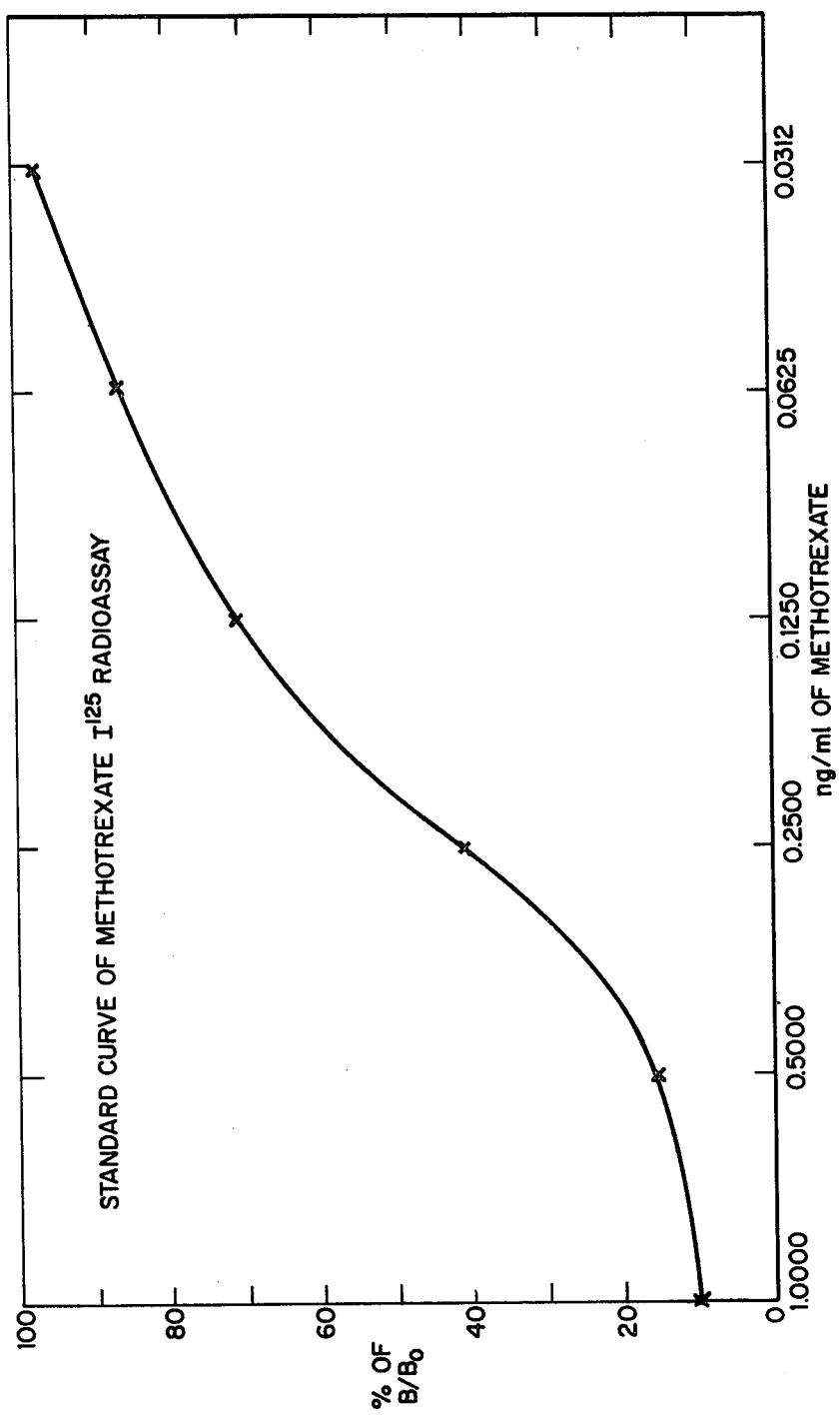

RADIOASSAY KIT FOR METHOD OF DETERMINING METHOTREXATE

This is a continuation of application Ser. No. 650,690, filed Jan. 20, 1976, now U.S. Pat. No. 4,043,759.

BACKGROUND OF THE INVENTION

Methotrextae is an antineplastic and immunosuppressive agent useful, for example, in the chemotherapy treatment of leukemic meningitis, osteogenic sarcoma, psoriasis and other disorders and malignancies in animals and man. Methotrexate is an antagonist to folic acid.

The drug methotrexate competitively inhibits the enzyme dihydrofolate reductase. The conversion of dihydrofolate to tetrahydrofolate is necessary for the biosynthesis of thymidylic acid, a precursor of DNA. Inhibition of dihydrofolate reductase by methotrexate blocks the DNA synthetic pathway and is selectively lethal to rapidly dividing cells.

The use of methotrexate in systemic and intrathecal, as well as conventional and high-dose drugs, therapy requires that the drug be carefully monitored to avoid clinical toxicity to the patient, and to permit the introduction of a rescue agent like leucovorin before the critical toxicity level is reached. Methotrexate is eliminated by the patient with time; however, the elimination rate often varies markedly in some patients. Toxicity can arise from the delayed elimination of the drug by the patient. Thus, a rapid, simple and accurate technique and system for determining the lever of methotrexate is important.

Present techniques for the monitoring of methotrexate in biological fluids are not wholly satisfactory, since such techniques are often complex, time-consuming and of limited availability. Some present suggested methods to assay methotrexate levels include: an enzyme-inhibition assay; radioimmunoassay, a fluorometrical method, and the use of a tritium radiolabeled drug.

One radioassay technique (see Raso and Schreiber, *Cancer Research* 35, 1407, June 1975) employs a tritium-labeled methotrexate, and uses a human serum buffer system with an enzyme from leukemia cells in a sequential assay technique, with the enzyme added first to the methotrexate sample.

Another radioassay technique, the Myers et al system (see Myers, Lippman, Eliot and Chabner, *Proc. Nat. Acad. Sci. USA*, Vol. 72, No. 9, pp 3683–3686, Sept. 1975, Medical Sciences), employs a competitive protein binding assay using tritium-labeled methotrexate, and uses a heparin buffer system and plasma samples.

SUMMARY OF THE INVENTION

Our invention relates to a method and apparatus for the determination of methotrexate. In particular, our discovery concerns a competitive binding radioassay method and kit for the quantitative determination of methotrexate in biological fluids employing a methotrexate $I^{125}$ derivative.

We have discovered a radioassay method and have developed a combination of materials in kit form to determine methotrexate, particularly for the in vitro determination of methotrexate concentration levels in biological fluids, such as, but not limited to, blood serum, plasma, cerbrospinal fluid and urine. Our method is sensitive to methotrexate levels as low as about 0.03 nanograms per milliliter (ng/ml); for example, in the 0.05 to about 1.0 ng/ml range, and will detect blood serum levels down to 0.6 ng/ml or $1.1 \times 10^{-9}$ moles/liter. The upper range limit of detection can be increased by suitable dilution or by adjusting the ratio of enzyme to the labeled methotrexate, so that, if necessary or desirable, the upper range limit of sensitivity can be increased up to a saturated methotrexate solution. In the determination of methotrexate in biological fluids, sensitivity in the range of 0.05 to 0.5 ng/ml is typically effective.

Our method is sensitive, rapid with results typically within 20 to 30 minutes, simple with easy-to-follow known laboratory procedures, and accurate with low cost. Our method is based on the competitive binding of $I^{125}$ labeled and unlabeled methotrexate to the enzyme dihydrofolate reductase. In our method, samples, such as biological fluids, containing unknown levels of methotrexate, which levels are to be determined, are mixed with a buffered solution containing known quantities of $I^{125}$ labeled methotrexate. Known quantities of competitive binding enzymes, such as a dihydrofolate reductase, are added, which competitively bind to a portion of the total labeled and unlabeled methotrexate present in the solution. Unbound methotrexate is then removed, such as by adsorption of the unbound methotrexate, with an adsorbent material, and the removal by centrifuging of the free absorbed drug and the adsorbent material, to provide a supernatant liquid essentially free of the free or unbound methotrexate.

Typically, a protein-coated particular adsorbent material, such as a dextran and/or hemoglobin-treated fine particles of charcoal, is used to remove the free drug. Although our technique amd method may be used, other methods are also adaptable; for example, liquid chromatography, ion-exchange resins and ultrafiltration.

The level of the bound derivative-labeled $I^{125}$ methotrexate in the supernatant liquid is then determined, employing a means to measure the radioactivity of the $I^{125}$ in the sample, such as by a gamma counter. The methotrexate level of the unknown samples tested is then calculated by comparison of the displacement of the bond labeled methotrexate caused by the unknown samples to the displacement caused by known levels of methotrexate concentration standards. Typically, the determination may be made by comparison with a standard plot curve or standard data table.

The labeled methotrexate employed in our method is a $I^{125}$ isotope having a half-life of about 60.0 days. The labeled $I^{125}$ methotrexate is supplied in derivative form, with the methotrexate in a solution (the $I^{125}$ derivative compound reacted with MTX). The labeled $I^{125}$ methotrexate is supplied with the kit apparatus in an organic solvent to prevent freezing, such as in an aqueous water-soluble material, such as dimethyl formamide solution. Water can be added to the solution to obtain the desired gamma count.

Our radioassay kit for use in the determination of methotrexate by out method comprises a buffer solution A and a buffer solution B component for use in preparing standard data, which are admixed prior to use to provide a buffered solution of a protein. However, human plasma and serum can be employed, although it is not recommended, since there is a risk of hepatitis. Preferably, the protein employed should be a nonhuman protein serum, such as an animal serum like and preferably bovine serum. The protein solution used is buffered at about a pH of 6.2, since this is the optimum pH for binding methotrexate to the enzyme dihydrofolate reductase, although, if desired, other pH ranges may be used.

Typical solutions A and B are: Buffer A — 500 ml of disstilled water — 0.15M phosphate buffer pH 6.2 with a peservative, such as 0.05% sodium azide; and Buffer B — a 10% bovine serum in Buffer A pH 6.2. The kit also includes an aqueous solution of a methotrexate standard at 100,000 ng/ml; a labeled methotrexate $I^{125}$ in 50% dimethyl formamide of approximately 2 $\mu$Ci; a dextran and gelatin-coated charcoal particles; a TPNH enzyme dihydrofolate reductase (prepared from L. casei by New England Enzyme Center, Boston, Massachusetts) and cotton swabs for use in the method.

Our methotrexate radioassay kit and our method for determining methotrexate will be described in their preferred embodiments for the purpose of illustration. However, it is recognized and is a part of our apparatus, kit and method and is within the spirit and scope of our invention that various changes and modifications can be and may be made by those persons skilled in the art to our apparatus and method.

BRIEF DESCRIPTION OF THE DRAWING

The drawing shows a standard semilog curve obtained by our radioassay method, relating the level of methotrexate to the ratio $B/B_o$, representing the ratio of the standard count (B) to the zero count (Bo) of the labeled $I^{125}$ methotrexate.

DESCRIPTION OF THE EMBODIMENTS

An anqueous solution of 1.5 M of a sodium phosphate buffer with 0.5% sodium azide in the amount of 50 ml is added to sufficiently distilled water to made 500 ml of buffered solution (Buffer A). A known amount of bovine serum (250–280 mg) Buffer B component is dissolved in 40 ml of distilled water and is added to 360 ml of Buffer A to provide a buffered bovine serum (Buffer B) for use in preparing the standard data.

A 50% water 50% dimethyl formamide solution of 2 ml of a methotrexate $I^{125}$ derivative (approximately 2$\mu$Ci) is admixed with 8 ml of Buffer A. The solution should be light-protected and held cold while using and stored at 4° C. The solution has about 19,000 cpm/100 ml. A methotrexate standard solution is provided for use which contains a known amount of methotrexate 100,000 ng/ml which, like the labeled solution, should be stored at 4° C and be light-protected. An amount of 2.5 grams of finely divided dextran-gelatin-treated charcoal is provided and prior to use added to 50 ml of distilled water and stored at 4° C as a charcoal suspension. A known amount of enzyme dihydrofolate reductase from L. casei 0.02 units (micromoles of dihydrofolate reduced/min.), when ready to be used, is admixed in a vial with 10 ml cold Buffer A with vigorous mixing. Patient samples to be tested should be protected from light, since methotrexate in dilute solution is light-sensitive.

The preparation of methotrexate standards is by serial dilutions of the 100,000 ng/ml stock in Buffer B as follows:

| | | | | |
|---|---|---|---|---|
| (a) | 100,000 ng/ml | 100 $\mu$l $\longrightarrow$ | 0.9 ml | (10,000 ng/ml) |
| (b) | 10,000 ng/ml | 100 $\mu$l $\longrightarrow$ | 0.9 ml | (1,000 ng/ml) |
| (c) | 1,000 ng/ml | 100 $\mu$l $\longrightarrow$ | 0.9 ml | (100 ng/ml) |
| (d) | 100 ng/ml | 100 $\mu$l $\longrightarrow$ | 0.9 ml | (10 ng/ml) |
| (e) | 10 ng/ml | 0.6 ml $\longrightarrow$ | 5.4 ml | (1 ng/ml) |
| (f) | 1 ng/ml | 3.0 ml $\longrightarrow$ | 3.0 ml | (0.5 ng/ml) |
| (g) | 0.5 ng/ml | 3.0 ml $\longrightarrow$ | 3.0 ml | (0.25 ng/ml) |
| (h) | 0.25 ng/ml | 3.0 ml $\longrightarrow$ | 3.0 ml | (0.125 ng/ml) |
| (i) | 0.125 ng/ml | 3.0 ml $\longrightarrow$ | 3.0 ml | (0.0625 ng/ml) |
| (j) | 0.625 ng/ml | 3.0 ml $\longrightarrow$ | 3.0 ml | (0.031 ng/ml) |

The preparation of patient samples, such as patient serum and spinal fluid, is as follows:

1. Take 0.3 ml of fluid to be tested and add to 2.7 ml Buffer B to provide a 1:10 dilution. If methotrexate concentration in original sample is between 0.5 and 10.0 ng/ml, it will be detected with this dilution.

2. Take 0.3 ml of 1:10 dilution and add to 2.7 ml of Buffer B to provide a 1:100 dilution. If methotrexate concentration is between 5 and 100 ng/ml, it will be detected in this dilution.

3. Take 0.3 ml of 1:100 dilution and add to 2.7 ml Buffer B to provide a 1:1000 dilution. If methotrexate concentration is between 50 and 1000 ng/ml, it will be detected in this dilution.

4. Take 0.3 ml of 1:1000 dilution and add to 2.7 ml Buffer B to provide 1:10,000 dilution. If methotrexate concentration is between 500 and 1,000 ng/ml, it wll be detected in this dilution.

This dilution sequence is repeated as required.

In our method, a sample of biological fluid containing an unknown amount of methotrexate to be determined is removed from the patient and is diluted 1:10 to 1:100 or as required to permit comparison to the standard curve in a buffered animal serum solution.

The procedure to be followed for the determination of methotrexate and to obtain a standard curve of FIG. 1 is as follows:

1. Dispense duplicate 1 ml aliquots of appropriately diluted patient samples (or of each dilution if range is unknown) or methotrexate standards (where standard curve is to be prepared) into each of 2 disposable test tubes.

2. Dispense 1 ml of Buffer B into each of 4 tubes (two for a blank and two for zero concentration).

3. Accurately dispense 100 $\mu$l of methotrexate $I^{125}$ solution to each tube to obtain a count of about 16,000 to 19,000 cpm.

4. Accurately dispense 100 $\mu$l of enzyme solution to each tube except blank. Shake briefly and allow tubes to stand at least 5 minutes to provide sufficient time for the competition of the labeled $I^{125}$ and unlabeled methotrexate with the known enzyme to take place. Times of 2 to 3 minutes have been found to be too short, while over 5 minutes; e.g., 5 to 10 minutes, are preferred.

5. Add 0.2 ml of charcoal-dextran suspension to each tube (charcoal should be well suspended before adding). Shake tubes well and allow to stand 7 to 10 minutes with occasional shaking.

6. Centrifuge for 1 or 2 minutes at 2500 X g. Centrifuging collects the dextran-charcoal adsorbent on which the free drug is bonded and removes the unbonded labeled $I^{125}$ and unlabeled drug from the solution.

7. Decant supernate liquid into clean tubes. Wipe last drop with swab from tube mouth and add swab to supernate.

8. Determine radioactive count per minute in supernate liquid employing a gamma counter or other means.

The calculation for the preparation of a standard curve or the compilation of standard data and the determination of the methotrexate level of the unknown samples are based on the competition of the labeled and unlabeled methotrexate in binding the enzyme. The $I^{125}$ radioactive isotope has a half-life of 60.0 days, and thus, after assembly and preparation of the kit components, the kit should be used typically within 30 days from the birth date of the isotope $I^{125}$ used. The kit typically states on the label — storage at 4° C, and gives the expiration date of use for the labeled and unlabeled methotrexate.

The preparation of the standard curve is plotted from data obtained, employing the known serial dilution amounts of methotrexate. A standard curve as in FIG. 1 was obtained from the data of Table I and plotted as the percent of the ratio $B/B_o$ on the ordinate to the amount of methotrexate in ng/ml on the abscissa. $B/B_o$ is defined as the log concentration vs.

$$\frac{\text{standard count} - \text{blank}}{\text{zero count} - \text{blank}}.$$

The sample count is then converted to $B/B_o$; that is, $$\frac{\text{sample count}}{\text{zero count}},$$

and the results compared to the standard curve to determine the level of methotrexate in the sample. The methotrexate concentration can be calculated by multiplying the results from the standard curve (or extrapolating or interpolating the standard date) by the dilution factor, and conversion to moles/liter is made by multiplying ng/ml by $2.2 \times 10^{-9}$.

TABLE I

| Methotrexate Standard Curve | | |
|---|---|---|
| Concentration of Methotrexate (ng/ml) | Counts per Minute | B/Bo × 100 |
| Blank | 1033 | — |
|  | 1268 |  |
| 0 | 6209 | 100 |
|  | 6879 |  |
| 0.031 | 6494 | 97.5 |
|  | 6327 |  |
| 0.0625 | 5699 | 80.3 |
|  | 5907 |  |
| 0.125 | 4972 | 70.7 |
|  | 4960 |  |
| 0.250 | 3297 | 42.2 |
|  | 3556 |  |
| 0.500 | 2006 | 15.1 |
|  | 1925 |  |
| 1.000 | 1705 | 10.4 |
|  | 1715 |  |

Table II shows an example of the determination of methotrexate concentration in patient's serum as determined by our method as a function of time from injection of the methotrexate into the patient.

TABLE II

| Example of Methotrexate Concentration in Patient Serum as Function of Time | | | | |
|---|---|---|---|---|
| Time after Injection | Dilution Factor | Counts per Minute | B/Bo × 100 | Concentration of Methotrexate (ng/ml) |
| After infusion | | 4706 | 82.25 | $6.6 \times 10^4$ |
| 24 hours | $10^6$ | 4861 | | |
|  | $10^5$ | 4748 | 78.3 | $7.2 \times 10^3$ |
|  |  | 4555 |  |  |
| 48 hours | $10^3$ | 2581 | 25.7 | 420 |
|  |  | 2446 |  |  |
| 63 hours | $10^3$ | 2890 | 36.2 | 290 |
|  |  | 3000 |  |  |
| 72 hours | $10^3$ | 3690 | 50.0 | 200 |
|  |  | 4002 |  |  |

Table III shows an example of the percent recovery of methotrexate by our method when added to cerebrospinal fluid, with the amount added being 100 ng/ml (0.1 ml to 0.9 ml spinal fluid).

TABLE III

| Dilution Factor | Concentration Expected (ng/ml) | cpm | B/Bo × 100 | Concentration Recovery | % Recovery |
|---|---|---|---|---|---|
| 100 | 1.0 | 1759 | 11.9 | 0.95 | 95 |
|  |  | 1826 |  |  |  |
| 200 | 0.5 | 2602 | 27.1 | 0.38 | 76 |
|  |  | 2620 |  |  |  |
| 1000 | 0.1 | 5399 | 78.0 | 0.093 | 93 |
|  |  | 5282 |  |  |  |

Our method and radioassay kit for the determination of methotrexate in biological fluids permit the rapid determination of methotrexate levels with a concise, easy-to-follow lab procedure, and avoid many of the difficulties and disadvantages associated with past methods of methotrexate determination.

What is claimed is:

1. A methotrexate radioassay kit for the determination of methotrexate in biological fluids by the competitive binding of $I^{125}$ labeled and unlabeled methotrexate to the enzyme dihydrofolate reductase, and the determination of the methotrexate in the sample by comparison of displacement of the bound-labeled methotrexate to the displacement by known methotrexate standards, which kit comprises in containers:

a. an aqueous buffer solution containing a buffering agent for a pH at which the determination is to be carried out;
   b. a serum solution adapted to be mixed with the buffered solution to provide, prior to use, a buffered serum solution for determining standard data on known methotrexate levels;
   c. a solution of a labeled $I^{125}$ methotrexate derivative adapted to be added in known quantities to the sample and to obtain standard data;
   d. a solution containing a known amount of methotrexate which is adapted to be diluted by the buffered solution for the preparation of standard data;
   e. a solution of the enzyme dihydrofolate adapted for addition in known amounts to the sample and known methotrexate to prepare standard data, and for competitive binding with known amounts of $I^{125}$ methotrexate in the sample; and
   f. a particulate sorbent material which is adapted to sorb preferentially free unbound methotrexate, whereby the amount of methotrexate in a biological fluid sample may be determined.

2. The kit of claim 1 wherein the sorbent material is a gelatin-, dextran- or hemoglobin-treated charcoal particulate material.

3. The kit of claim 1 wherein the serum is bovine serum.

4. The kit of claim 1 wherein the labeled $I^{125}$ methotrexate is in aqueous, water-soluble, organic, solvent solutions.

5. The kit of claim 1 wherein the buffer solution contains a phosphate buffer for a pH of about 6.2.

6. A methotrexate radioassay kit for the determination of methotrexate in biological fluids by the competitive binding of $I^{125}$ labeled and unlabeled methotrexate to the enzyme dihydrofolate reductase, and the determination of the methotrexate in the sample by comparison of displacement of the bound-labeled methotrexate to the displacement by known methotrexate standards, which kit comprises in containers:
   a. an aqueous buffer solution containing a phosphate buffering agent for a pH of about 6.2 at which the determination is to be carried out;
   b. a nonhuman serum solution adapted to be mixed with the buffered solution to provide, prior to use, a buffered serum solution for determining standard data on known methotrexate levels;
   c. an aqueous, water-soluble, organic solvent solution of a labeled $I^{125}$ methotrexate derivative adapted to be added in known quantities to the sample and to obtain standard data;
   d. a solution containing a known amount of methotrexate which is adapted to be diluted by the buffered solution for the preparation of standard data;
   e. a solution of the enzyme dihydrofolate adapted for addition in known amounts to the sample and known methotrexate to prepare standard data, and for competitive binding with known amounts of $I^{125}$ methotrexate in the sample; and
   f. a gelatin-, dextran- or hemoglobin-treated, charcoal, particulate sorbent material which is adapted to sorb preferentially free unbound methotrexate, whereby the amount of methotrexate in a biological fluid sample may be determined.

7. The kit of claim 6 wherein the serum is bovine serum.

8. The kit of claim 6 wherein the solvent solution is an aqueous-dimethyl formamide solution.

* * * * *